United States Patent [19]

Bradley et al.

[11] Patent Number: 4,585,507
[45] Date of Patent: Apr. 29, 1986

[54] APPARATUS FOR MAKING ELASTIC DIAPERS

[75] Inventors: John J. Bradley; John R. Merkatoris, both of Green Bay, Wis.

[73] Assignee: Paper Converting Machine Company, Green Bay, Wis.

[21] Appl. No.: 718,234

[22] Filed: Apr. 1, 1985

Related U.S. Application Data

[63] Continuation-in-part of Ser. No. 565,227, Dec. 27, 1983, Pat. No. 4,543,141.

[51] Int. Cl.⁴ .............................................. A61F 13/16
[52] U.S. Cl. .................................. 156/461; 156/164; 156/201; 156/465; 156/494
[58] Field of Search .............................. 156/201–204, 156/164, 229, 494, 495, 461, 465, 467

[56] References Cited

U.S. PATENT DOCUMENTS

| | | | |
|---|---|---|---|
| 3,853,668 | 10/1974 | Onishi | 156/461 |
| 4,300,967 | 11/1981 | Sigl | 156/164 |
| 4,353,762 | 10/1982 | Bouda | 156/229 X |
| 4,543,141 | 9/1985 | Bradley et al. | 156/164 |

*Primary Examiner*—David Simmons
*Attorney, Agent, or Firm*—Tilton, Fallon, Lungmus & Chestnut

[57] ABSTRACT

Apparatus for producing elastic disposable diapers employing an oscillating fork means to V-fold longitudinally spaced portions of an adhesive equipped ribbon on itself to immobilize the adhesive in the spaced portions.

7 Claims, 6 Drawing Figures

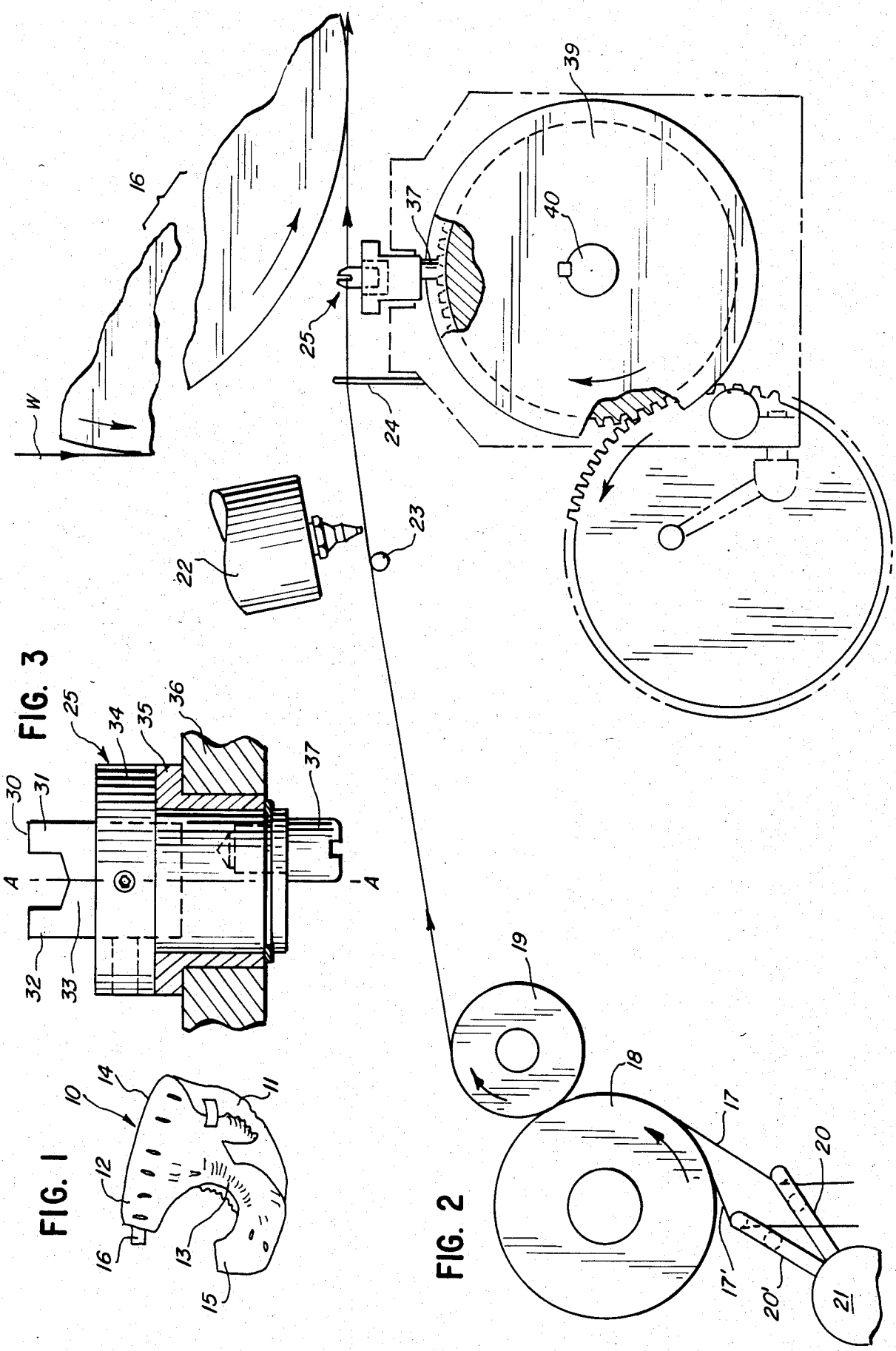

FIG. 5 — RIBBON CONFIGURATION

FIG. 6 — FORK ROTATION PROGRAM

APPARATUS FOR MAKING ELASTIC DIAPERS

This is a continuation-in-part under Public Law 98-622, of Bradley and Hansen application, Ser. No. 565,227, filed Dec. 27, 1983, now U.S. Pat. No. 4,543,141.

BACKGROUND AND SUMMARY OF INVENTION

This invention relates to apparatus for making elastic diapers and, more particularly, to apparatus wherein discrete portions of the elastic ribbon are V-folded to limit the amount of puckering of the diaper.

The basic teaching for the manufacture of an elastic leg band diaper is found in U.S. Pat. No. 4,081,301 and consists of stretching the elastic ribbons, maintaining tension therein, and intermittently applying adhesive to selected portions of the elastic corresponding to the contractable leg portion of the diaper. Intermittent operation of devices used for applying adhesives is commonly accepted—but requires adhesives within a fairly narrow range of viscosity since the adhesive must be responsive to on-off operation of the nozzles or other applying means. Because the adhesive in such a situation must be fluid enough to be responsive, it lacks the higher tack characteristic of more desirable adhesives having higher viscosity. These more desirable adhesives, if used in on-off situations, cause plug-up and stringing problems, require sensitive heat control and expensive applying devices.

However, limiting the length of ribbon adhered to the underlying web results in that only selected portions of the diaper are shirred or gathered when the ribbon tension is relaxed. Further, the non-glued portions of the ribbon due to being unattached, do not cause gathering and also, upon relaxation of tension, retreat to normal length and are hidden inside the diaper.

On the other hand, with adhesives having higher viscosities and therefore higher tack, which could be used if the adhesive stripe were put down continuously, the deleterious effects of creep or slippage on the long term storage exposure to higher temperatures are avoided. However, the prior art expedients relative to continuous glue application involve either much higher cost materials or the addition of a release medium which must also be placed on the substrate intermittently.

For example, U.S. Pat. No. 4,300,967 teaches the use of a thermoplastic elastomeric material for the continuous ribbon and requires special equipment including heated rolls, chill rolls, etc., to immobilize or render inert spaced portions of the adhesive equipped elastic ribbon which correspond to the ends of the diaper.

U.S. Pat. No. 4,353,762 teaches the use of a release medium applied to intermittent spaced portions of the moisture impervious web while the adhesive is applied continuously to the stretched ribbon. Thereafter, the ribbon adheres almost instantaneously to the impervious web but will not adhere to those portions covered with the release medium. However, this again requires complicated equipment and the expenditure of additional money for materials not needed. In both cases, there is a "canceling out" of the activity of the adhesive.

SUMMARY OF THE INVENTION

The invention in Ser. No. 565,227, now U.S. Pat. No. 4,543,141, departed from the previous expedients in not performing some additional expensive and complicated operation to "cancel out" the activity of the adhesive, but rather used the adhesive itself to achieve non-adherence in longitudinally spaced portions of the underlying moisture impervious web. More particularly, after the continuous stripe of adhesive had been laid down on the flat ribbon, intermittent portions were "V-folded", i.e., folded longitudinally on itself to provide longitudinally spaced portions of ribbon which were incapable of adherence to the underlying web. In that broad aspect, the instant invention is identical. However, the instant invention differs from that of Ser. No. 565,227 in the means for carrying out the V-folding of the adhesive-equipped ribbon.

In Ser. No. 565,227, now U.S. Pat. No. 4,543,141, the folding was carried out by a wheel having a circumferential groove of varying width which brought about selective V-folding. Such apparatus performed adequately but not optimally because on occasion excess adhesive on the ribbon about to be folded could be entrapped in the circumferential groove and thus detract from proper folding.

This drawback has been avoided according to the instant invention through the use of oscillating fork means. More particularly, the fork means includes a support having upstanding fold-producing members flanking the path of travel of the adhesive-equipped ribbon. The support itself is mounted for rotation about a generally vertical axis and means are provided for oscillating the support rapidly through an acute angle from a first position where the members flank the path to a second position where the members contact the ribbon to fold it on itself and, after a predetermined time, rapidly counter-rotating the support to the first position to provide a discrete length of folded ribbon.

The invention is described in conjunction with an illustrative embodiment in the accompanying drawing, in which FIG. 1 is a perspective view of a diaper made according to the teachings of this invention;

FIG. 2 is a fragmentary side elevational view, partially in section, featuring the elements of the apparatus employed in the practice of the invention;

FIG. 3 is an enlarged fragmentary side elevational view, partially in section of the central right hand portion of FIG. 2 and featuring the oscillating fork means;

FIGS. 5 and 6 are graphs showing, respectively, the ribbon configuration achieved through the practice of the invention and the fork rotation program.

DETAILED DESCRIPTION

Figure 4:
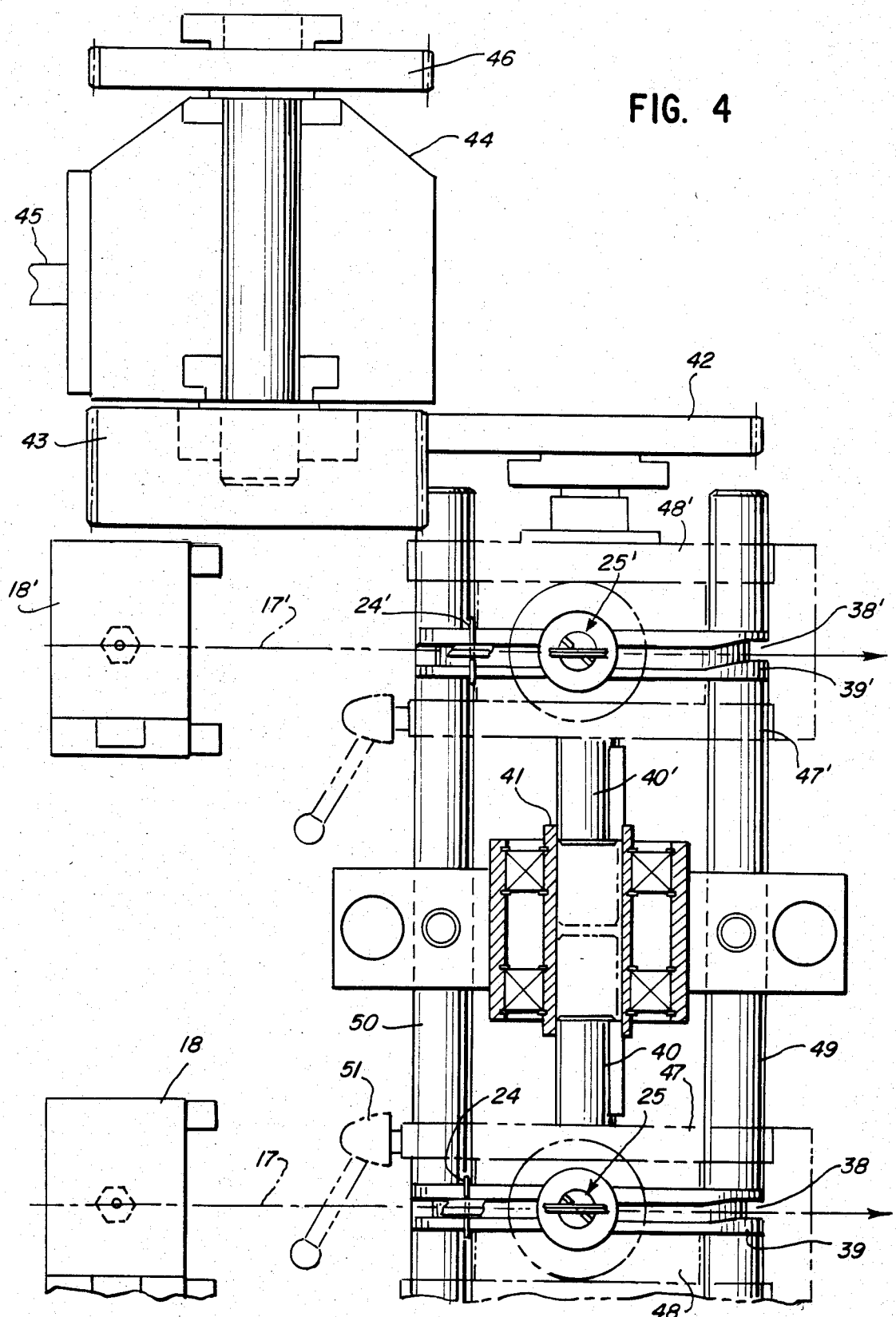
FIG. 4 is a fragmentary top plan view, partially in section of the apparatus seen in FIG. 2.

The goal of the invention is to provide a disposable diaper of the character seen in FIG. 1 and designated generally by the numeral 10. The diaper 10 includes an outer moisture impervious layer 11 and an inner moisture previous layer 12—usually constructed of nonwoven material. The outer web 11 is normally constructed of polyethylene. Sandwiched between the layers 10 and 11 is a batt of absorbent material. The details of construction and general manufacture can be found in the already-mentioned application Ser. No. 565,227 and reference is hereby expressly made to the same.

In the diaper 10, the central or crotch portion 13 is puckered or shirred whereas the end portions at 14 and 15 which are intended to lie against the infant's waist and back are unpuckered. Normally tape tabs at 16 are employed to secure the end portions 14 and 15 together.

The puckered or shirred portion 13 is achieved by adhering a stretched elastic ribbon to the central portion of the diaper length and upon severing of the ribbon adjacent the diaper ends 14, 15, the elastic ribbons contract to develop the puckering. Inasmuch as the ribbons are not secured in the end portions 14, 15, there is no puckering in those areas.

OPERATION GENERALLY

Referring now to FIG. 2, the symbol W in the upper right hand portion designates a polyethylene web which is one of the raw materials used to make the diaper. The web W is fed into the apparatus around a chill roll 16 which supports the web while two leg elastic ribbons 17, 17' are joined to the web with glue. The elastic ribbons 17, 17' are fed into the machine by four elastic feed rolls, two of which are seen in the lower left hand portion of FIG. 2. The elastic feed roll 18 is a driven roll while the elastic feed roll 19 is an idler. A similar pair of rolls are provided for the web 17'—the roll 18' being seen in the central left hand portion of FIG. 4.

The feed rolls supply elastic at a slower rate than the feed of web W which creates tension in the leg elastics between the feed rolls and the chill roll 16. The elastic strands 17, 17' are provided from a source (not shown) and pass through eye bolts 20, 20' see the lower left hand portion of FIG. 2, the eye bolts 20, 20' being supported on a stationary cross shaft 21.

A glue extruder 22—see the central portion of FIG. 2—is provided for the elastic ribbon 17 and a similar extruder (not shown) is provided for the ribbon 17'. The extruders operate to place a line or stripe of glue on each elastic leg ribbon, approximately in the center of the elastic which is typically about ¼" wide. It is possible however that with wider elastics, of the order of about ½" width, two or three glue lines may be employed and such can be advantageously achieved by the instant inventive apparatus.

Just ahead of the glue application, the elastics are supported and guided by guide rods as at 23 relative to the ribbon 17. These serve to steady and support the elastics during glue application. Shortly after glue application, the elastics pass through guides 24 and 24' (see also the central portion of FIG. 4) which serve to keep the elastics tracking in a straight line and flat when entering the oscillating fork means 25, 25'.

The fork means oscillate according to the program profiled in FIG. 6 to develop the ribbon pattern or configuration illustrated in FIG. 5. In FIG. 5, for example, there is an unfolded portion designated 26 and a folded portion designated 27. To achieve this, the fork means 25, 25', as the case may be, oscillate from an open configuration as seen at 28 and which corresponds to that seen in FIG. 3—to a partially closed configuration or orientation as illustrated at 29 and which is illustrated in FIG. 4 at 25, 25'. There, the fork means is rotated from being exactly perpendicular to the path of travel of the ribbons 17, 17'.

DETAILS OF OSCILLATING FORK MEANS

The rotating or oscillating forks are designed with a shallow V-shape at the bottom of the space between the two prongs of the fork. This shallow V-shape serves to start the V-folding action reliably, but it does not interfere with the adhesion of the elastic to the poly when the adhesion is required in the diaper being made. More particularly, as can be appreciated from a consideration of FIG. 3, the fork has a general U-shape 30 including upstanding members 31 and 32 connected across their lower ends by a bight portion 33. The fork means is mounted for rotation about a generally vertical axis as at AA in FIG. 3. It will be appreciated that the oscillating fork means is identical for each of the ribbon pads 17, 17' so, in the interest of economy of space, only one such oscillating fork means 25 will be described in detail.

The fork 30 consisting of the parts 31-33 is mounted in a rotating element 34. The rotating element 34 in turn is journalled within a bearing 35 carried by a portion 36 of the machine frame. Again, the frame has been omitted for clarity—in most web handling machines, a pair of side frames are employed which support the various transversely extending rolls and other operative elements. Such is the case with the instant invention.

Still referring to FIG. 3, it will be noted that the rotating element 35 is equipped with a cam follower stud 37 which is eccentrically located relative to the axis of rotation A—A. The cam follower stud 37 lies in the track 38 of a barrel cam 39—see the extreme lower right hand portion of FIG. 4. A corresponding cam 39' with its track 38' is provided for the oscillating fork means 25' as can be appreciated from the upper central portion of FIG. 4.

Thus, as the cams 39, 39' rotate (one revolution per diaper), the tracks 38, 38' move the followers 37, 37' to rotate the forks 30, 30'—and V-fold the leg elastic ribbons for that portion of their lengths where the adhesion of the ribbons to the poly is not wanted. The shape of the tracks 38, 38' in the cams 39, 39' controls the amount of elastic which is V-folded in each diaper.

CAM ROTATION MEANS

Referring now to the central right hand portion of FIG. 4, the cams 39 and 39' are seen to be mounted on and rotated by shafts 40 and 40'. These shafts are connected by means of a sleeve 41 which keeps the two shafts synchronized by means of sliding keys in a single keyway in sleeve 41. Gear 42 (see the upper right hand portion of FIG. 4) is mounted on shaft 40' to rotate both shafts and thereby both barrel cams 39, 39'. Gear 42 is driven by gear 43 (a wide-face gear) from a commercial differential phase shifter 44.

The purpose of the phase shifter 44 is to provide means for the machine operator to change and control the location of the V-folded portion of the elastics within the diapers being made. Turning control rod 45 (seen fragmentarily in the upper left hand portion of FIG. 4) changes the timing relationship between the rotary forks and the remainder of the machine. Gear 46 is driven from the machine via a gear (not shown) which causes the phase shifter to turn one revolution per diaper. The phase shifter is conveniently positioned to provide easy access for the operator to turn the phase shifter control rod 45 and thus vary the location of the V-folded portion of the elastics within the diapers being made.

OSCILLATING FORK MEANS SUPPORT

The structural elements providing immediate support for the rotating fork means 25, 25' can also be seen in FIG. 4 where they are represented by dashed lines. For example, the rotating fork assembly 25 and its associated cam 39 and shaft 40 are mounted in their own subframe assembly 47, 48. These subframe assemblies 47, 48 are mounted on stationary shafts 49 and 50 which in turn are mounted on the machine frame. Each subframe assembly has a clamp screw and handle as at 51 to secure it to the shaft 50. The purpose of this feature is to provide means for changing and adjusting the distance between leg elastics as diaper designs and specifications change. The glue extruder 22, guides 23 and supports 24 are also mounted on the subframe assemblies.

The gear 43 has a wide face so that axial adjustment of the subframes 47, 48, 47', 48' and its associated shaft 40' and gear 42 will maintain gears 42 and 43 in driving relation.

In operation, the fork means 25, 25' are rotatable about the axis AA bisecting the slot defined by the upstanding members 31, 32. Rotation in one direction of the order of 60°–70° develops the advantageous V-fold to bring the face halfs of the ribbon into adhering relation. Rotation of the fork means in the opposite direction to "re-open" the slot results in the ribbon being flat again. The bottom of the slot in the fork means 25, 25' is advantageously concavely shaped as shown which promotes the tendency of the fork to fold the ribbon.

We claim:

1. Apparatus for applying an elastic ribbon to a web in the manufacture of disposable diapers and the like comprising a frame and means on said frame for advancing said web toward a ribbon uniting station, a source for said ribbon operably associated with said frame, means on said frame for advancing said ribbon from said source along a predetermined path toward and into said station, adhesive applying means in said path for applying a continuous stripe of adhesive to said ribbon, oscillator fork means on said frame in said path between said adhesive applying means and said station arranged to selectively fold said ribbon on itself at longitudinally spaced portions to selectively prevent adherence of said ribbon portions to said web, said web advancing means and said ribbon advancing means being so related as to develop tension in said ribbon at said uniting station.

2. The apparatus of claim 1 in which said fork means includes a support having upstanding fold producing members flanking said path, said support being mounted on said frame for rotation about a generally vertical axis, and means on said frame for oscillating said support through an acute angle.

3. The apparatus of claim 2 in which said oscillating means includes means for rapidly rotating said support from a first portion where said members flanking said path to a second position where said members contact said ribbon to fold it on itself and, after a predetermined time, rapidly counter rotating said support to said first position to provide a discrete length of folded ribbon.

4. The apparatus of claim 3 in which said acute angle between said first and second positions is of the order of about 60° to about 80°.

5. The apparatus of claim 3 in which said oscillating means includes a cam follower stud mounted on said support eccentric to said axis and barrel cam means rotatably mounted on said frame and being equipped with a cam follower groove for receipt of said stud.

6. The apparatus of claim 3 in which said frame is equipped with phase shifter means for altering the location of said discrete length of folded ribbon relative to said web.

7. The apparatus of claim 6 in which said oscillating means includes a cam follower stud mounted on said support eccentric to said axis and barrel cam means rotatably mounted on said frame and being equipped with a cam follower groove for receipt of said stud, first gear means on said frame for rotating said barrel cam means, second gear means operably associated with said means for advancing said web, said phase shifter means being interposed between said first and second gear means.

* * * * *